United States Patent [19]
Reid et al.

[11] Patent Number: 5,972,987
[45] Date of Patent: Oct. 26, 1999

[54] METHOD FOR REMOVING NITS FROM HAIR

[75] Inventors: Lori Fox Reid, Dayton, Tenn.; Robert D. Kross, Bellmore, N.Y.

[73] Assignee: Lori Fox Reid, Dayton, Tenn.

[21] Appl. No.: 09/270,350

[22] Filed: Mar. 16, 1999

[51] Int. Cl.$^6$ .......................... A61K 49/00; A61K 33/00; A61K 31/61; A61K 31/415

[52] U.S. Cl. .......................... 514/407; 424/9.1; 424/600; 424/607; 424/646; 424/647; 424/648; 424/653; 514/163; 514/454; 514/680; 514/764

[58] Field of Search .......................... 424/9.1, 600, 607, 424/646, 647, 648, 653; 514/163, 407, 454, 680, 764

[56] References Cited

U.S. PATENT DOCUMENTS

| | | | |
|---|---|---|---|
| 4,439,427 | 3/1984 | Bernstein | 514/139 |
| 4,927,813 | 5/1990 | Bernstein | 514/65 |
| 5,292,504 | 3/1994 | Cardin et al. | 514/65 |
| 5,380,756 | 1/1995 | Andrews et al. | 514/731 |
| 5,547,665 | 8/1996 | Upton | 424/94.61 |
| 5,658,750 | 8/1997 | Sheftel et al. | 435/29 |
| 5,681,859 | 10/1997 | James et al. | 514/625 |

OTHER PUBLICATIONS

Arnold Mallis–Handbook of Pest Control, Sixth Edition, Franzak & Foster Company, pp. 593–595, 1982, Month Not Available.

*Primary Examiner*—Kathleen K. Fonda
*Attorney, Agent, or Firm*—Pitts & Brittian, P.C.

[57] ABSTRACT

A method for removing lice eggs from the hair of an infested human or animal using a nit-visualizing composition. The composition involves the use of certain dyes which have an affinity to the surface of nits, to thereby enable a second individual to more easily see and remove the eggs during a combing or other removal process. To effectuate this purpose, a colored material is dispersed within a water- or alcohol-based solvent and, in one embodiment, a liquefied propellant as well. The composition is applied to the hair of the infested human or animal, and then removed after drying by a process of brushing or washing. However, the colored material which adsorbs to the chitinous exoskeleton and binding cement of the lice eggs remains on the nits, thereby facilitating visual identification and removal of the lice eggs from hair.

23 Claims, No Drawings

METHOD FOR REMOVING NITS FROM HAIR

TECHNICAL FIELD

This invention is directed to nit-visualizing compositions and their method of use for facilitating the removal of lice eggs from human and animal hair. More specifically, the present invention is directed to the application to an individual's head of certain dyes which have an affinity to the surface of the nit, to thereby enable a second individual to more easily see and remove the eggs during a combing process.

BACKGROUND ART

Lice infestation of the human body is an enduring problem of the ages, with reference being made to these pests throughout recorded history. As noted by Cardin, et al., in U.S. Pat. No. 5,292,504, the spread of typhus has been attributed to lice, decimating both armies and navies of the 15th through 18th centuries. Even today lice present a source of serious health problems worldwide. Not only do lice carry a variety of bacteria on their outer surfaces, but in their fecal matter as well. Lice transmit bacteria to the human host through puncture wounds inflicted during feeding. U.S. Pat. No. 5,547,665 issued to Upton reveals that lice infestation can cause such ailments as staphylococcal skin infections, typhus, trench fever and relapsing fever.

The human lice genus includes head-, body-, and pubic lice, each of which has specific characteristics in their habitat and feeding. Lice are capable of spreading rapidly. A fertilized female lays about six to eight eggs every 24 hours. It has been estimated that a single female louse and her daughters could have 112,778 offspring in a period of 48 days. The present invention is of primary use in the elimination of the eggs (nits) of head lice.

The head louse (*pediculus humanus capitis*) clings to the hair shaft when feeding, mating and laying eggs. Removal of nits is particularly difficult, as each nit is cemented to a shaft of hair by a glycoprotein glue, acting as a binding cement. Lice eggs themselves are covered by a chitinous sheath which surrounds both the nit and the attached hair shaft. Thus, removal of nits requires separation from individual shafts of hair.

Various methods and compositions for the removal of head lice from hair are known. Certainly, the manual removal of lice through the use of a fine-toothed comb or tweezers has been employed for years. In addition, a number of insecticides (known in this application as pediculicides) have been developed for killing lice, thereby substantially alleviating reproduction. Pediculicides, such as lindane and various pyrethrins, have been used in conjunction with shampoos for killing and rinsing out lice. However, as noted by Upton in U.S. Pat. No. 5,547,665, the use of these methods and compositions is not entirely effective in controlling head lice, as some lice often survive the treatment. Indeed, the National Pediculosis Association has reported that 20 to 80 percent of nits survive initial pediculicide treatment, resulting in reinfestation.

Pyrethrum, permethrin and lindane pesticides, the only FDA approved pesticides for lice, all work as central nervous system (CNS) toxins on lice. Their effectiveness depends on their ability to reach the functioning CNS of lice. Unfortunately, lice eggs do not develop a functioning CNS until they are between three and four days old, during an average incubation period of approximately ten days. As a result, only 60% to 70% of eggs treated can be killed upon application of one of these pesticides. The only absolutely certain method for eliminating a lice infestation is the removal of all remaining eggs after treatment.

Adding to the difficulty of removing nits is their virtually microscopic size, and the fact that the color of their keratinous shell tends to blend into the subject's hair and scalp background. Thus, nits can be extremely difficult not only to remove, but even to locate.

In recent years several compositions have been developed which are claimed to swell the nit around the hair shaft in order to facilitate removal by combing. One such patent is U.S. Pat. No. 4,927,813 issued to Bernstein. This patent employs the noxious agent formic acid in a pharmaceutically—acceptable carrier applied to a patient's hair and scalp for a period of time sufficient to effect swelling. This application is followed by washing and rinsing in order to remove the detached nits. The distributors of one such commercial product, containing 8% formic acid, has reported that five minutes of combing after treatment has led to a 93.5% removal of nits. While impressive, the remaining 6.5% nits remain viable and could potentially reproduce rapidly and reinfest the subject.

A more recent patent, U.S. Pat. No. 5,547,665 issued to Upton discloses a water-based enzyme composition which causes swelling and/or biodegrading of the complex organic cement that binds nits to hair in order to facilitate their removal. Whether or not this enzyme composition is completely effective in causing swelling of all nits, it is still contemplated that the loosened nits would be physically removed from the host following application of the enzyme, by a process of combing or nit-picking. Thus, these inventions do not completely remove the difficulty in locating and extracting nits from the subject's hair.

U.S. Pat. No. 5,658,750, issued to Sheftel, discloses methods for detecting louse infestations and monitoring the course and effectiveness of pediculicide treatments. This involves removal of hair samples containing nits or suspected nits themselves and subjecting the removed materials to a vital indicator to provide a visual, colorimetric indication of their viability. In one embodiment, the degree of color change of the isolated material indicates the degree of cell viability, and in another embodiment, a color is preferentially taken up by either live or dead cells in contrast to the other. This method, however, will only characterize the viability of those nits that are removed with excised hair samples, from which only conjecture can be made about the viability of the remaining nits. Further, without removal of copious hair samples from many different parts of the head, the method leaves considerable doubt about the potential for reinfestation.

It should also be noted that the prior art, even in disclosing methods of killing head lice, does not solve the historical problem of manually removing even dead lice or nits. It is self evident that the continuing presence of large numbers of even dead nits can be emotionally distressing to both the patient and his or her family. Further, the process of manually removing nits is tedious, time consuming, and potentially even painful.

Other methods have been produced to aid in the removal of head lice. Typical of the art are those devices disclosed in the following U.S. Patents:

| U.S. Pat. No. | Inventor(s) | Issue Date |
|---|---|---|
| 4,439,427 | Bernstein | March 27, 1984 |
| 5,292,504 | Cardin, et al. | March 8, 1994 |
| 5,380,756 | Andrews, et al. | January 10, 1995 |
| 5,681,859 | James, et al. | October 28, 1997 |

Again, these devices in no way facilitate the visible detection of nits so as to ease the process of physical removal.

The present invention results from efforts to devise some means to ensure the complete removal of nits from hair, whether pretreated by pediculicide or not, in order to reduce to a small probability that such nits will remain undetected on the scalp or hair and subsequently reinfest the patient. While pretreatment of the scalp with an agent that loosens nits from the hair shaft may facilitate their removal by subsequent combing, where the comb must contact each such nit-bearing hair shaft, it is obvious that without such contact the nit will most likely remain on the hair. This fact lead to our search for agents which can preferentially target the nits and in some manner enable them to be visually discerned against the subject's hair and scalp background. With this accomplished, the comber could individually detect and efficiently remove each of the nits.

The desired agents must have a specific affinity for the chitinous, poly (N-Acetyl-D-Glucosamine) shell of the nit and/or the binding cement, and less so for the keratinous, protein hair shaft, in order to provide the differentiation. Additionally, the desired agents should be readily visible at the low concentrations in which they would be present on the tiny nit surface, following some suitable method of application. A further requirement would be their dermal and respiratory safety, at the concentrations at which they would be applied to the subject in some suitable solubilizing and/or suspending medium. The resulting invention, described below, satisfies these needs and provides additional advantages which shall become apparent.

Objects of the Invention

It is, therefore, an object of the present invention to provide compositions which can be applied to the subject to enable nits on hair to be better visualized in order to facilitate the removal process.

It is a further object of the present invention to identify those visualants which have high perceptibility at low concentrations, and which are characterized by an affinity to nit surfaces and/or the binding cement, so that they may be seen against the background of the patient's scalp and a diversity of hair colorations.

It is an additional object of the present invention to identify compositions which are safe to humans and have sufficient solubilities and safe solvents to enable them to be applied to humans without harm.

In addition, it is an object of the present invention to provide safe compositions which serve as visualants for nits, but which can easily be rinsed from the hair and scalp of the subject so as to avoid the embarrassment of an unwanted coloration.

It is a further object of the present invention to provide a method for the removal of nits which involves the easy and safe application of compositions which serve as visualants for nits so as to facilitate their removal.

It is finally an object of the present invention to augment the success of nit-softening agents designed for nit removal by enabling nits to be seen by an individual attempting to complete their physical removal and, therefore, greatly minimize the probability of reinfestation.

DISCLOSURE OF THE INVENTION

These and other objects and advantages of the present invention will be accomplished, as revealed by the description which follows.

The present invention relates to the discovery of a group of brightly colored dyes which have preferential adsorptive affinities to either or both the chitin surface of a nit or the binding cement, such that when applied to the hair of an infested individual the enhanced visibility of the nits facilitates their physical removal. In a preferred embodiment, the dyes are certain fluorescent dyes which have the requisite solubilities in appropriate dispensing solvents and which possess well-known safety profiles. In addition, the dyes must manifest superior intensities when adsorbed onto nit surfaces so as to be perceptible against the backdrop of skin and hair shafts. Finally, the dyes must be readily removable from skin and hair, irrespective of color or shade, while at the same time remaining adsorbed to nit surfaces.

The dyes are generally applied to the scalp hair of persons or animals who have first been treated with a pediculicide to kill the viable lice within the hair mass. It is preferably applied, in addition, to those subjects whose hair has been subsequently exposed, postpediculicide, to a nit-loosening composition, such as an aqueous enzyme- or formic-acid preparation. The visualizing solution is generally applied as a spray, although it may also be used as a rinse, with particular attention to the base areas of the hair shafts. When used as a spray the solution may be delivered under pressure, using propellants and solvents, and mixtures thereof, of suitable volatility and solubilizing characteristics. When the solution is delivered as a non-pressurized spray, the solvent system generally requires an overall greater volatility than for the pressurized application, part of which medium transforms rapidly to vapor.

After a brief evaporation period, following application of the dye solution, the non-absorbed bulk of the excess dye composition should be removed. A preferred method of removal is simply by brushing the dried material from the hair. The color brushes out of the subject's hair, but not from the nits. Thus, the nits are more easily identified.

After removal of the excess dye, the nit removal process commences. This is preferably by means of either a fine-toothed comb or tweezers, under normal daylight or incandescent light, with the dyed nits being readily visible in contrast to the surrounding hair and scalp. In the preferred method, even greater contrast may be obtained by carrying out the procedure under fluorescent light or, even more so, ultraviolet ("black") light, where the nits appear to glow.

According to another aspect of the invention, a kit is provided that will allow an individual to carry out a complete home treatment for the remediation of lice infestation and nit removal. The kit includes a pediculicide shampoo, a nit-loosening composition, a spray container of visualizing dye, a fine-toothed comb, and instructions how to use the kit.

BEST MODE FOR CARRING OUT THE INVENTION

The term "subject" is used throughout the specification as including any human or animal to whom treatment with the compositions and methods according to the present invention is administered. The invention primarily contemplates the treatment of humans in home settings, but animals treated in home and veterinary settings are also within the scope of the present invention.

The term "effective concentration" or "effective amount" is used to describe an amount or concentration of an agent, such as the visualizing dye, or dye solution, or other additives included in the present invention to produce an intended effect. For example, in the case of the visualizing dye, the amount of the dye used in the present invention is that amount which is effective for substantially enhancing the visibility of the nit on the hair shaft, but can vary considerably in its concentration in the liquid phase, which can comprise a variety of other additives as well as both solvent and propellant (when present), depending on the amounts of such additives and the absolute and relative volumes of both solvent and propellant.

The term "dyes" is used to describe all coloring materials, either organic or inorganic, that are capable of being dissolved or dispersed in carrier solvents and liquid media. The term "fluorescent dyes" is used to describe all dyes and pigments which produce visible light of one coloration as a result of exposure to and absorption by radiations of different wavelength. This can include the pleochromic minerals which can selectively absorb various wavelengths of light and display different colors when looked at in the directions of the different crystal axes.

The term "dissolved" is used to describe the full dissociation of a solid or liquid material and its subsequent distribution into the surrounding medium, as well as the dispersion of such materials in a finely particulated form in such media such that the particles, while not fully dissolved, remain effectively and uniformly dispersed in the media. The term "solution" is used to describe true solutions as well as dispersions, and combinations thereof.

The typical process for removing head lice from a subject first involves application of a pediculicide, such as lindane or pyrethrins. Pediculicides are generally available either as a cream or within a shampoo. Following application of the pediculicide, the hair is then meticulously combed to remove remaining eggs. This physical removal process is important to avoid reinfestation, as pediculicides often will not destroy every one of the nits. Unfortunately, the removal process is quite difficult as lice eggs are typically laid near the base of the hair shafts, with each nit being encircled around the hair shaft by a tenacious cement substance. Moreover, the nits are tiny and very difficult to see, particularly as viewed against the similarly-colored scalp.

The present invention provides a visualizing liquid hair treatment containing certain dyes which have an affinity for the chitinous surface of lice eggs (nits), particularly head lice (*pediculus humanus capitis*), and the binding cement. The resulting coloration of the nits facilitates their easier detection during a physical removal process, such as combing. The inventive dye treatment of the present invention furnishes ready visibility to ensure that the comber and comb can make appropriate visual and physical contact, respectively.

The inventive compositions comprise various dyes which were discovered to have a particular combination of characteristics which render them suitable for nit visualization. First, the dyes demonstrate preferential adsorptive tendencies towards a) the outer nit shell, which is composed of the carbohydrate derivative poly(N-acetyl-D-glucosamine), and/or b) the binding cement, in comparison to the protein-based keratin of hair, such that brushing of hair to which dye has been applied to remove excess dye enhances the visual contrast of the nit and the hair. Second, the dyes have appropriate solubilities or dispersibilities in solvents and non-aqueous and aqueous mixtures thereof, in combination with liquid propellants if delivered in a pressurized spray, such that much of the liquid in the spray application of the dye solutions will evaporate more rapidly than would water solutions alone.

Among the dyes which are suitable for nit visualization are thimerosal (sodium ethylmercurithiosalicylate), Methyl Blue (sodium triphenyl-p-rosanilinetrisulfate), Brilliant Green (Malachite Green G) and Tartrazine (FD&C Yellow No. 5). Many of these are members of the class of dyes known as the triphenylmethanes, xanthenes, anthraquinones and pyrazolones, which generally are considered to be suitable color-imparting materials for this invention. Also useful in this invention are the so-called "pearlescent pigments," which generally comprise combinations of mica and such other color-imparting materials as bismuth oxychloride, ferric ammonium ferrocyanide, and iron oxide.

In a preferred embodiment, the inventive compositions comprise certain members of the class of xanthene dyes, primarily the fluorescein dyes. These include fluorescein [9-(o-carboxy)-6-hydroxy-3H-xanthen-3-one], also known as D&C Yellow No. 7; its disodium salt, also known as D&C Yellow No. 8; and various halogen derivatives of fluorescein, which have the requisite high visual detectability at low nit-surface concentrations to serve as visualizing agents. Included in the preferred fluorescein family is the compound known as Mercurochrome [2',7' Dibromo-4'-(hydroxymercurio)-fluorescein, disodium salt]; Eosin Y [sodium tetrabromofluorescein]; D&C Red No. 28 [2', 4', 5', 7', tetrabromo 4, 5, 6, 7, tetrachlorofluorescein, disodium salt]; and FD&C Red #3 [2', 4', 5', 7', tetraiodofluorescein, disodium salt]. While the fluorescein dyes are preferred, those skilled in the art will understand that dyes of other colors, including white, may be used, so long as they impart suitable contrast between the nits and the background scalp and hair colors.

The level of inclusion of the dye, or dyes, in the visualizing compositions in order to achieve an effective concentration is dependent upon many factors, including the amount and nature of the solvents, whether or not propellants are used, the inherent intensity of the dye, and the presence and nature of such other optional ingredients as plasticizers, lubricants and fragrances. Typically, dyes are used at levels from about 0.001% to about 0.50% in the liquid visualizing solution, preferably from about 0.05% to about 0.20%.

Solvents which have shown value in the practice of this invention include water, ethyl alcohol, ispropyl alcohol, acetone, triethanolamine and dimethyl ether, and combinations thereof. Propellants of value are those liquids which have boiling points approximating and lower than ambient temperatures, including but not limited to isobutane, propane, freons, volatile silicones, chloroform, methylene chloride, and dimethyl ether. The last four materials can be categorized as both solvents and propellants, and serve in the latter capacity when the inventive solutions are dispensed from pressurized solutions. Solvents, in the absence of propellants, are employed in the range from about 85% to about 99.9% of the compositions, preferably from about 90% to about 99%. In the presence of propellants, the combined levels of solvents and propellants also exists in the range from about 85% to about 99.9% of the compositions, preferably from about 90% to about 99%. Of this total liquid combination, the propellants represent from about 10% to about 90% of the whole, when measured under pressure such that all propellants are liquefied,.

Those skilled in the art will realize that additional materials may be included in the inventive compositions in order to provide or enhance certain properties of the compositions.

One such additive is a lubricant to facilitate movement of the comb through the subject's hair. Suitable lubricants include silicone compositions such as the "Silwets," lanolin and its derivatives, and mineral oil.

Another optional material is a plasticizer or an emollient. These additives provide suppleness and texture to the hair. Plasticizers and emollients can include such materials as diethyl phthalate, dioctyl sebacate and polyglyceryl oleate.

Polymers may also be included in the composition of the present invention. Polymers are used to add body to the hair. PVP/PVA copolymer, polyvinyl propionate, melamine formaldehyde resins, polyacrylamide, and the methane-sulfonic acid derivative thereof are appropriate polymer compositions for use in these inventive compositions.

Finally, those skilled in the art will recognize the optional use of fragrances so as to contribute a pleasant aroma to the compositions.

The method of applying the disclosed compositions is generally by means of a spray apparatus, most often after the subject has been treated with a pediculicide shampoo and, optionally a nit-loosening treatment. Directly before application of the spray, irrespective of preceding treatment, or no treatment, the hair should be no more than slightly moist, as would be achieved by towel drying. In the preferred method of application, the composition is applied to dry hair by means of an aerosol spray container.

Also, prior to application to the subject's hair in a well ventilated area, a towel or cloth should be placed over the shoulders to protect skin and clothes. The face should either be covered or care should be taken to avoid spray contact with the eyes, ears, nose and mouth. A further recommended precaution is to place a cotton strip around the subject's hairline to prevent drippage onto the facial features and neck. The individual applying the disclosed compositions should also wear protective gloves, such as disposable plastic gloves, to avoid skin contact and subsequent staining.

The spray application, to be most effective, is at a distance of about 6 inches, and in short bursts. Areas of application for humans should be directed where nits are likely to be concentrated, including the nape of the neck, the area behind and above the ears, across the crown, and down the center line of the head. Prior to each burst, the hair should be parted to the scalp to permit contact of the delivered spray to nits at the base of the hair shafts. This process of parting and spraying is continued until all areas of the hair on the head have been appropriately treated.

Following application of the disclosed compositions, the solvents are allowed to evaporate for a period of time which depends upon the volatility of the component solvents. A typical evaporation period is 30 seconds to 5 minutes. A residual moistness of the hair is appropriate, although not necessary. The composition is then removed from the subject's hair shafts, preferably by a process of combing, brushing or toweling. Removal of the dye composition more easily enables one to see the nits within the subject's hair, so as to facilitate physical removal.

The preferred method for removing the nits from the subject's hair involves use of a fine-toothed comb under strong illumination. The preferred illuminating source is a fluorescent light, although any light, including natural light and incandescent light, is effective. Supplementation with a "black-light" (an ultraviolet lamp) is also helpful, but requires protective glasses to prevent eye damage to the comber and subject. Combing of the hair is most efficient when the subject's hair is divided into small sections, preferably 1 square inch (6.5 square cm.) or less, with each section being combed individually. Each stroke should begin as close to the scalp as possible. The comb is then moved slowly down the length of the hair shafts at a slight backward angle. With each stroke, the person removing the nits must visually verify that the comb has removed the colored nits, and repeat each section, if necessary, to ensure complete removal. This is particularly important in those areas behind the ears and nape of the neck. It is also recommended that the comb be intermittently wiped on an alcohol-dampened tissue so as to reduce the chances of reinfestation of another hair section.

After the nit removal process is complete, the hair may be shampooed with warm water to remove any further residual coloration.

Having generally described the invention, reference is now made to the following examples which are intended to illustrate the inventive compositions in their preferred embodiments. In the following examples, unless otherwise noted, all parts and percentages in the examples, as well as the instant disclosures and claims, are understood to be by weight.

EXAMPLE 1

This example illustrates a nit-visualizing fluorescent spray composition intended to be dispensed from a pressurized spray container. Prepare the following concentrate, A, by sequentially dissolving the individual ingredients in the ethyl alcohol solvent.

| Component | Level (wt %) |
| --- | --- |
| Ethanol (anhydrous, SDA-40) | 92.4 |
| PVP/VA copolymer, 70/30 | 4.5 |
| Isopropyl myristate | 1.2 |
| Perfume oil | 1.2 |
| Silicone fluid 556 | 0.40 |
| Eosin Y | 0.30 |

Cool the solution to about −15° C., and add 1 part of the liquid to 2 parts of the following liquefied propellant, B, (at about −25° C.):

| Component | Level (wt %) |
| --- | --- |
| Dimethyl ether | 75.0 |
| Isobutane | 25.0 |

Fill the mixed liquid into the base of a suitable pressurizable container, to the specified level, insert the valve assembly, and seal the top by crimping. The final composition in the pressurized container is:

| Component | Level (wt %) |
| --- | --- |
| Dimethyl ether | 50.00 |
| Isobutane | 16.67 |
| Ethanol (anhydrous) | 30.80 |
| PVP/VA copolymer | 1.50 |
| Isopropyl myristate | 0.40 |
| Perfume oil | 0.40 |
| Silicone fluid | 0.13 |
| Eosin Y | 0.10 |

This composition, when sprayed on the hair, will facilitate visualization of nits on hair shafts by imparting a bright pink coloration to the nits, which fluoresces yellow, and which can be removed from the hair after nit removal with a warm-water shampoo.

EXAMPLE 2

The composition designated as "A" in Example 1 is introduced into a pump spray container, without the addition of the propellant mixture "B." The resulting device may be used in the same manner as the pressurized container of Example 1, to achieve the same effect.

EXAMPLE 3

This example provides a nit-visualizing colored composition comprising a blue pigment and a blue dye which, when sprayed onto lice-infested hair, will facilitate their visual detection and thereby their physical removal. Prepare the following concentrate, C, by sequentially dissolving or dispersing the indicated materials in the ethyl alcohol solvent.

| Component | Level (wt %) |
| --- | --- |
| Ethanol (anhydrous, SDA-40) | 87.8 |
| Blue pigment* | 5.0 |
| (in melamine/formaldehyde resin) | |
| PVP/VA/vinyl propionate copolymer | 4.5 |
| Diethyl phthalate | 1.2 |
| Fragrance oil | 1.2 |
| FD&C Blue #1 | 0.30 |

*—Comprising Chroma-Lite Dark Blue, containing mica, bismuth oxychloride and ferric ammonium ferrocyanide. Such pigments may also include iron oxide and titanium dioxide.

Cool the suspension to about −15° C., and add 1 part of the liquid to 2 parts of the liquefied propellant B, shown in Example 1, at about −25° C. Fill the mixed liquid into the base of a suitable pressurizable container, to the specified level, insert the valve assembly, and seal the top by crimping. The final composition in the pressurized container is:

| Component | Level (wt %) |
| --- | --- |
| Dimethyl ether | 50.00 |
| Isobutane | 16.67 |
| Ethanol (anhydrous) | 29.27 |
| Blue pigmented melamine/ | 1.66 |
| formaldehyde resin | |
| PVP/VA/vinyl propionate copolymer | 1.50 |
| Diethyl phthalate | 0.40 |
| Fragrance oil | 0.40 |
| FD&C Blue #1 | 0.10 |

This composition, when sprayed on the hair, will facilitate visualization of nits on hair shafts by imparting a deep blue coloration to the nits, and which can be removed from the hair after nit removal with a warm-water shampoo.

EXAMPLE 4

The composition designated as "C" in Example 3 is introduced into a pump spray container, without the addition of the propellant mixture "B." The resulting device may be used in the same manner as the pressurized container of Example 3, to achieve the same effect.

From the foregoing description, it will be recognized by those skilled in the art that a Nit-Visualizing Composition, and Method for Removing Nits From Hair offering advantages over the prior art has been provided. Specifically, the Nit-Visualizing Composition of the present invention enables one to more easily locate lice eggs from the hair of an infested subject, so as to facilitate removal of lice and eliminate infestation.

While a preferred embodiment has been shown and described, it will be understood that it is not intended to limit the disclosure, but rather it is intended to cover all modifications and alternate methods falling within the spirit and the scope of the invention as defined in the appended claims. Various modifications or changes that may be made to that described hereinabove by those of ordinary skill in the art are also contemplated by the present invention and are to be included within the spirit and purview of this application and the following claims.

Having thus described the aforementioned invention, We claim:

1. A method for identifying and removing lice eggs from the hair of an infested human or animal comprising the steps of:

applying a nit-visualizing composition to the hair of the infested human or animal, said nit-visualizing composition comprising:
a solvent which represents about 85% to about 99.9% of said nit-visualizing composition by weight; and
a colored material dispersed in said solvent, said colored material capable of being adsorbed to the chitinous exoskeleton and binding cement of lice eggs thereby facilitating visual identification and removal of the lice eggs from hair, and wherein said colored material may be removed from the hair without removing said colored material from the chitinous exoskeleton and binding cement of the lice eggs; and removing the identified lice eggs from the hair of the infested human.

2. The method for identifying and removing lice eggs of claim 1 further comprising the step of removing said nit-visualizing composition from the hair of the infested human or animal before removing the identified lice eggs.

3. The method for identifying and removing lice eggs of claim 2 wherein said nit-visualizing composition is applied to the hair of the infested human or animal by means of a spray container.

4. The method for identifying and removing lice eggs of claim 3 wherein said nit-visualizing composition is placed under pressure in said spray container, and wherein said nit-visualizing composition further comprises a liquefied propellant combined with said solvent, said liquefied propellant and said solvent together representing about 85% to about 99.9% of said nit-visualizing composition by weight when under pressure.

5. A method for removing lice eggs from the hair of an infested human or animal, said method comprising the steps of:

applying a nit-visualizing composition to the hair of the infested human or animal by means of a pressurized spray container, said nit-visualizing composition comprising, under pressure:
a liquefied propellant representing about 10% to about 90% by weight of said nit-visualizing composition;
a solvent, said solvent and said liquefied propellant together representing about 85% to about 99.9% by weight of said nit-visualizing composition;
a lubricant;
a plasticizer;
a polymer;
a fragrance; and
a colored material dispersed in said liquefied propellant and said solvent, said colored material representing about 0.001% to about 0.50% by weight of said nit-visualizing composition, said colored material capable of being adsorbed to the chitinous exoskeleton and binding cement of lice eggs thereby facilitating visual identification and removal of the lice eggs from hair, and wherein said colored material may be removed from the hair of said human or animal without removing said colored material from the chitinous exoskeleton and binding cement of the lice eggs;

removing said nit-visualizing composition from the hair of the infested human or animal;

identifying the lice eggs in the hair of the infested human or animal; and removing the identified lice eggs from the hair of the infested human or animal.

6. The method of claim 1, 2, 3, 4, or 5 wherein said nit-visualizing composition is applied to the hair of an infested animal.

7. The method of claim 1, 2, 3, 4, or 5 wherein said nit-visualizing composition is applied to the hair of an infested human.

8. The method according to claim 4 or 5, wherein said liquefied propellant is chosen from the group consisting of isobutane, propane, freons, volatile silicones, chloroform, methylene chloride, and dimethyl ether.

9. The method in accordance with claim 4 or 5, wherein said solvent is chosen from the group consisting of water, ethyl alcohol, ispropyl alcohol, acetone, triethanolamine, and combinations thereof.

10. The method of claim 5, wherein said lubricant is chosen from the group consisting of silicone compositions, lanolin, lanolin derivatives, and mineral oil.

11. The method of claim 5, wherein said plasticizer is chosen from the group consisting of diethyl phthalate, isopropyl myristate, dioctyl sebacate and polyglyceryl oleate.

12. The method of claim 5, wherein said polymer is chosen from the group consisting of PVP/PVA copolymer, polyvinyl propionate, melamine formaldehyde resins, polyacrylamide, and the methane-sulfonic acid derivative of polyacrylamide.

13. The method of claim 5, wherein said fragrance is a perfume oil.

14. The method according to claim 3, 4, or 5, wherein said colored material is a soluble dye.

15. The method of claim 14, wherein said soluble dye is chosen from the group consisting of triphenylmethanes, xanthenes, anthraquinones and pyrazolones.

16. The method of claim 14, wherein said soluble dye is chosen from the group consisting of thimerosal (sodium ethylmercurithiosalicylate), Methyl Blue (sodium triphenyl-p-rosanilinetrisulfate), Brilliant Green (Malachite Green G), and Tartrazine (FD&C Yellow No. 5).

17. The method of claim 14, wherein said soluble dye is a fluorescein dye.

18. The method according to claim 14 wherein said soluble dye is chosen from the group consisting of fluorescein [9-(o-carboxy)-6-hydroxy-3H-xanthen-3-one], also known as D&C Yellow No. 7, its disodium salt, also known as D&C Yellow No. 8, Mercurochrome [2',7' Dibromo-4'-(hydroxymercurio)-fluorescein, disodium salt], Eosin Y [sodium tetrabromofluorescein], D&C Red No. 28 [2', 4', 5', 7' tetrabromo 4, 5, 6, 7 tetrachlorofluorescein, disodium salt], and FD&C Red #3 [2', 4', 5', 7', tetraiodofluorescein, disodium salt].

19. The method according to claim 3, 4 or 5 wherein said colored material is a pigment.

20. The method according to claim 19 wherein said pigment is a pearlescent pigment chosen from the group consisting of mica, bismuth oxychloride, ferric ammonium ferrocyanide, iron oxide and titanium dioxide.

21. The method of claim 5 further comprising the steps of:

applying a pediculicide to the hair of the infested human or animal;

removing the pediculicide from the hair of the infested human or animal; and drying the hair of the infested human or animal; and wherein:

said liquefied propellant is a combination of dimethyl ether representing about 50.00% by weight, and isobutane representing about 16.67% by weight;

said solvent is anhydrous ethanol representing about 30.80% by weight;

said lubricant is silicone fluid;

said plasticizer is isopropyl myristate;

said polymer is PVP/PVA copolymer;

said fragrance is perfume oil, representing about 0.40% by weight; and said colored material dispersed in said liquefied propellant and said solvent is eosin Y, said colored material representing about 0.10% by weight of said nit-visualizing composition.

22. The method of claim 5 further comprising the steps of:

applying a pediculicide to the hair of the infested human or animal;

removing the pediculicide from the hair of the infested human or animal; and drying the hair of the infested human or animal; and wherein:

said liquefied propellant is a combination of dimethyl ether and isobutane, said dimethyl ether representing about 50.00% by weight, and said isobutane representing about 16.67% by weight of said nit-visualizing composition;

said solvent is anyhydrous ethanol representing about 29.97% by weight;

said plasticizer is diethyl phthalate, representing about 0.40% by weight;

said polymer is PVP/VA/vinyl propionate copolymer, representing about 1.50% by weight;

said fragrance is perfume oil, representing about 0.40% by weight; and said colored material dispersed in said liquefied propellant and said solvent is a combination of blue pigmented melamine/formaldehyde resin representing about 1.66% of said nit-visualizing composition by weight, and FD&C Blue dye #1 representing about 0.10% by weight of said nit-visualizing composition; and wherein said nit-visualizing composition does not contain a lubricant.

23. The method of claim 5, wherein said method for applying said nit-visualizing composition to the hair of an infested human or animal is by means of a pump spray container, and said solvent being chosen from the group consisting of water, ethyl alcohol, ispropyl alcohol, acetone, triethanolamine, dimethyl ether, and combinations thereof, said solvent representing about 85% to about 99.9% by weight of said nit-visualizing composition.

* * * * *